United States Patent [19]
Ward et al.

[11] Patent Number: 5,622,951
[45] Date of Patent: Apr. 22, 1997

[54] PIPERAZINE DERIVATIVES AS 5-HT ANTAGONISTS

[75] Inventors: Terence J. Ward, Reading; Mark A. Ashwell, Slough, both of England

[73] Assignee: John Wyeth & Brother Ltd., England

[21] Appl. No.: 436,413

[22] PCT Filed: Dec. 24, 1993

[86] PCT No.: PCT/GB93/02661

§ 371 Date: May 24, 1995

§ 102(e) Date: May 24, 1995

[87] PCT Pub. No.: WO94/15928

PCT Pub. Date: Jul. 21, 1994

[30] Foreign Application Priority Data

Jan. 6, 1993 [GB] United Kingdom ............... 9300194

[51] Int. Cl.$^6$ ............... A61K 31/405; C07D 403/04
[52] U.S. Cl. ............... 514/253; 544/295; 544/296; 544/360; 544/363; 544/364; 544/392; 514/254; 514/255
[58] Field of Search ............... 514/253, 254, 514/255; 544/295, 360, 392, 363, 364, 296

[56] References Cited

U.S. PATENT DOCUMENTS

| T100,505 | 4/1981 | Morrow et al. | 542/444 |
|---|---|---|---|
| 3,309,370 | 3/1967 | Schut et al. | 260/268 |
| 3,354,161 | 11/1967 | Schut et al. | 260/268 |
| 4,975,445 | 12/1990 | Caprathe et al. | 514/252 |
| 5,047,406 | 9/1991 | Caprathe et al. | 514/252 |

FOREIGN PATENT DOCUMENTS

| 2206094 | 6/1974 | France. |
|---|---|---|
| 2689893 | 10/1993 | France. |
| 1410303 | 10/1975 | United Kingdom. |

OTHER PUBLICATIONS

R. N. Schut et al., *Journal of Medicinal Chemistry* 15:3/ 301–304 (Mar. 1972).

Mokrosz, et al., Chemical Abstrats, vol. 119:282. Pol. J. Pharmacol. Pharm., 1992, 44(6), 595–607 1993.

Kleemann et al., Chemical Abstracts, vol. 81:49702. Ger. Offen. 2,255,439, 30 May 1974.

*Primary Examiner*—Joseph McKane
*Assistant Examiner*—Richard S. Myers, Jr.
*Attorney, Agent, or Firm*—R. F. Boswell, Jr.

[57] ABSTRACT

Piperazine derivatives of formula (I) and their pharmaceutically acceptable salts are 5-HT$_{1A}$ binding agents and may be used, for example, as anxiolytics. In the formula, R and R$^3$ are hydrogen or lower alkyl or R$^3$ is spirocycloalkyl, R$^1$ and R$^2$ are aryl or heteroaryl radicals and n is 1 or 2 and m is 1 to 3 and the total of n+m is 2–4.

7 Claims, No Drawings

PIPERAZINE DERIVATIVES AS 5-HT ANTAGONISTS

This application is A371 PCT/GB93/02661 filed Dec. 24, 1995.

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of the general formula

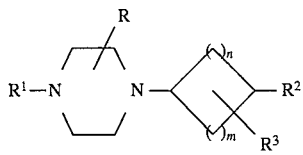
(I)

and the pharmaceutically acceptable acid addition salts thereof.

In formula (I)

R represents hydrogen or one or two same or different (lower)alkyl groups, $R^1$ and $R^2$ are each the same or different mono- or bicyclic aryl or heteroaryl radicals, $R^3$ represents hydrogen, one or two same or different (lower)alkyl groups or a spirocycloalkyl group and n is 1 or 2 and m is 1 to 3 and the total of n+m is 2, 3 or 4.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl.

When R and/or $R^3$ represents two same or different lower alkyl groups the two groups may be on the same or different carbon atoms. When $R^3$ represents a spirocycloalkyl group the cyclic alkane ring (i.e. the $R^3$ group together with the carbon atom to which it is attached) can contain, for example, from 3 to 7 carbon atoms.

When used herein "aryl" means an aromatic radical having 6 to 12 carbon atoms (eg phenyl or naphthyl) which optionally may be substituted by one or more substituents. Preferred substituents are lower alkyl, lower alkoxy (eg methoxy, ethoxy, propoxy, butoxy), halogen, halo(lower)alkyl (eg trifluoromethyl), nitro, nitrile, amido, (lower)alkoxycarbonyl, amino, (lower)alkylamino, di(lower)alkylamino, thio(lower)alkyl or phenyl substituents. Two substituents on the aromatic ring may be connected together to form another ring system. For example $R^1$ may be a bicyclic oxygen-containing radical of the formula

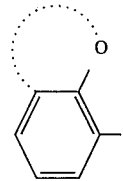

wherein the heterocyclic ring containing the oxygen atom contains a total of 5 to 7 ring members, said heterocyclic ring being saturated or unsaturated and optionally containing one or more hetero ring members (eg O, N or S) in addition to the oxygen atom illustrated and the bicyclic oxygen radical being optionally substituted by one or more substituents such as the substituents mentioned above in connection with "aryl". A preferred example of such a bicyclic oxygen radical is an optionally substituted radical of the formula

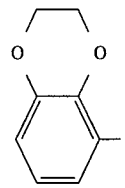

Preferably $R^1$ is a phenyl radical containing a substituent in the ortho position. A particularly preferred example of $R^1$ is o-(lower)alkoxyphenyl eg o-methoxyphenyl.

Preferably $R^2$ is phenyl, a substituted phenyl radical (for example alkyl-phenyl) pyridyl or alkyl substituted pyridyl.

The term "heteroaryl" refers to an aromatic radical containing one or more hetero atoms (eg oxygen, nitrogen, sulphur), which may be optionally substituted by one or more substituents and which is linked to the rest of the molecule via a carbon ring atom. Examples of suitable substituents for "heteroaryl" are given above in connection with "aryl" radicals. The heteroaryl radical may, for example, contain up to 11 ring atoms. Preferably the heteroaryl radical is a monocyclic radical containing 5 to 7 ring atoms or a bicyclic radical containing 8 to 11 ring atoms. Preferably the hetero ring contains a nitrogen hetero atom with or without one or more further hetero atoms. When $R^1$ is a heteroaryl group it is preferably an optionally substituted pyrimidyl, quinolinyl, isoquinolinyl, or indolyl radical. When $R^2$ is a heteroaryl group it is preferably pyridyl (eg 2- or 3-pyridyl optionally substituted by one or more lower alkyl and/or lower alkoxy groups), indolyl or oxadiazole optionally substituted by lower alkyl.

Preferred compounds have the following substituents either independently or in combination:

(a) n and m are both 2

(b) R is hydrogen (c) $R^1$ is o-methoxyphenyl (d) $R^2$ is phenyl or pyridyl optionally substituted by lower alkyl, (particularly 3,5-dimethylpyridin-2-yl)

(e) $R^3$ is hydrogen

The compounds of the invention can exist in various stereochemical forms. The compounds of the invention may be a mixture of cis and trans isomers or as separate cis and trans isomers. For example, when n and m are both 2 the $R^2$ group and the piperazine ring attached to the cyclohexane ring can be in either axial or equatorial configurations as respectively shown below

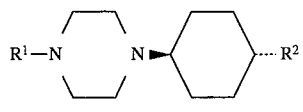

and

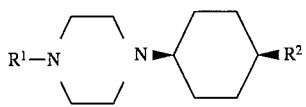

The equatorial configuration is preferred. The forms can be separated by for example, chromatography or fractional crystallisation.

The compounds of the invention may be prepared by methods known in the art from known starting materials or starting materials that may be prepared by conventional methods.

One method of preparing the compounds of the invention comprises reductively alkylating a piperazine of formula

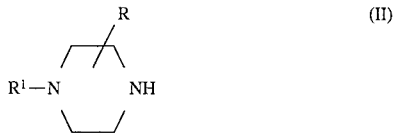

(where R and $R^1$ have the meanings given above) with a carbonyl compound of formula (III)

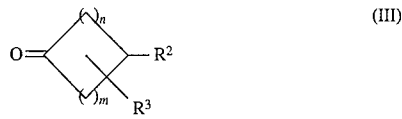

where m, n, $R^2$ and $R^3$ are as defined above. The piperazine and carbonyl compound can be condensed in presence of a reducing agent such as $NaBH_3CN$ or $NaBH(OAc)_3$.

A second process of preparing the compounds of the invention comprises reduction of a compound of formula (IV)

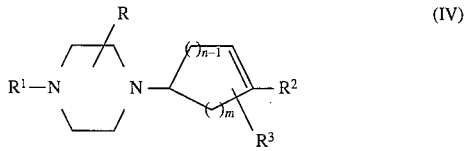

where R, $R^1$, $R^2$, $R^3$, n and m are as defined above. The reduction is preferably carried out by catalytic hydrogenation using, for example, a palladium catalyst.

The starting materials of formula IV can be prepared by known methods. For example a piperazine compound of formula (II) may be reductively alkylated with a carbonyl compound of formula (V)

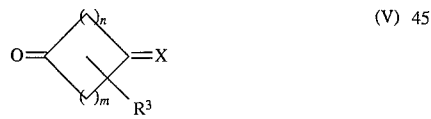

where n and m are as defined above and X is a protected oxo group (for example a ketalised oxo group, eg ethylenedioxy) to give a compound of formula (VI)

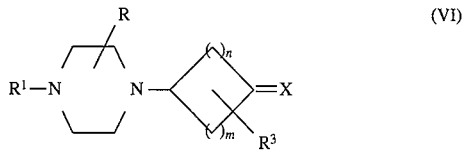

where R, $R^1$, $R^3$, X, n and m are as defined above. The reductive alkylation can be carried out by, for example, condensing the piperazine compound of formula (II) with the carbonyl compound of formula (V) in presence of a reducing agent eg $NaBH(OAc)_3$. The protecting group in the compound of compound (VI) can be removed, eg by acid hydrolysis, to give a compound of formula (VII)

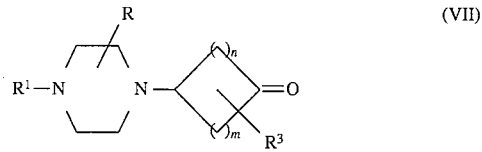

where R, $R^1$, $R^3$, n and m are as defined above. Reaction of the compound of formula (VII) with an organometallic compound eg a compound of formula $R^2M$ (where $R^2$ is as defined above and M is Li, MgHal or CeHal where Hal is halogen) gives a compound of formula (VIII).

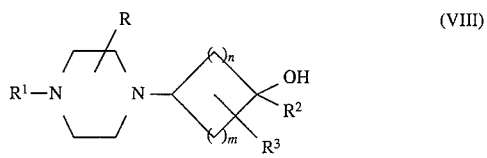

which may be dehydrated in the presence of a dehydrating agent to the compound of formula (IV). Examples of dehydrating agents include trifluoroacetic acid or preferably, especially when $R^2$ is heteroaryl, a lower alkyl oxalyl chloride (eg methyl oxalyl chloride) in presence of a base (eg imidazole).

The compound of formula (IV) may also be prepared by an alternative process which comprises reductively alkylating a piperazine of formula II with a carbonyl compound of formula (IX)

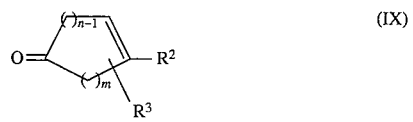

where $R^2$, $R^3$, n and m are as defined above. The reductive alkylation can be carried out by, for example, condensing the piperazine compound with the carbonyl compound in presence of a reducing agent, eg $NaBH(OAc)_3$.

A third process for preparing the compounds of the invention comprises reduction of a compound of formula (X)

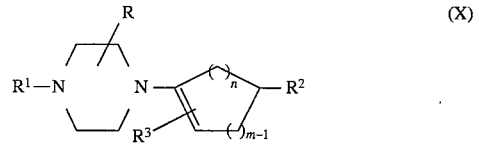

where R, $R^1$, $R^2$, $R^3$, n and m are as defined above. The reduction may be carried out, for example, with a hydride reducing agent (eg lithium aluminium hydride) or by catalytic hydrogenation (eg using a palladium catalyst). The compound of formula (X) may be prepared by condensation of compounds (II) and (III) under dehydrating conditions (eg using a Dean and Stark apparatus).

A fourth process for preparing the compounds of the invention comprises condensing a compound of formula (II) above with a compound of formula

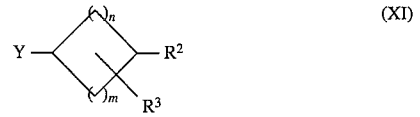

where n, m, $R^2$ and $R^3$ are as defined above and Y is a leaving group. Examples of leaving groups include halogen (eg chlorine) and organosulphonyloxy groups (eg methanesulphonyloxy or p-toluenesulphonyloxy).

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the present invention possess pharmacological activity. In particular, they act on the central nervous system by binding to 5-HT receptors. In pharmacological testing it has been shown that the compounds particularly bind to receptors of the $5\text{-HT}_{1A}$ type. In general, the compounds selectively bind to receptors of the $5\text{-HT}_{1A}$ type to a much greater extent than they bind to other receptors such as $\alpha_1$ and $D_2$ receptors. Many exhibit activity as $5\text{-HT}_{1A}$ antagonists in pharmacological testing. The compounds of the invention can be used for the treatment of CNS disorders. such as anxiety in mammals, particularly humans. They may also be used as antidepressants, antipsychotics, hypotensives and as agents for regulating the sleep/wake cycle, feeding behaviour and/or sexual function and for treating cognition disorders.

The compounds of the invention were tested for $5\text{-HT}_{1A}$ receptor binding activity in rat hippocampal membrane homogenate by the method of B S Alexander and M D Wood, J Pharm Pharmacol, 1988, 40, 888–891. The compounds of Example 1 (in the trans configuration) and Example 20 which are representative compounds of the invention, have $IC_{50}$ of respectively 0.6 nM and 1.6 nM in this procedure.

The compounds are tested for $5\text{-HT}_{1A}$ receptor antagonism activity in a test involving the antagonism of 5-carboxamidotryptamine in the guinea-pig ileum in vitro (based upon the procedure of Fozard et at, Br J Pharmac, 1985, 86, 601P). The compound of Example 1, in the trans form, had a $pA_2$ of 9.1.

Certain of the compounds of formula IV are novel compounds and possess pharmacological activity similar to that described above for the final products of formula (I). For example, the compound of Example 19 below has an $IC_{50}$ of 1.84 nM in the $5\text{-HT}_{1A}$ receptor binding procedure described above. Accordingly the present invention also provides 1-(2-methoxyphenyl)-4-[1-(3,5-dimethylpyridin-2-yl)cyclohex-1-en-4-yl]piperazine or a pharmaceutically acceptable acid addition salt thereof.

The invention also provides a pharmaceutical composition comprising a compound of formula I or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, glidants, compression aides, binders or tablet disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours. viscosity regulators, stabilisers or osmo-regulators. Suitable examples of liquid carriers for oral and parenteral administration include water (particularly containing additives as above, eg cellulose derivatives, preferably sodium carboxymethyl cellulose solution), alcohols (eg glycerol and glycols) and their derivatives, and oils (eg fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention.

EXAMPLE 1

Cis- and trans-1-(2-methoxyphenyl)-4-(1-phenylcyclohex-4-yl)piperazine

A mixture of 4-phenylcyclohexanone (1.74 g, 10 mmol), 1-(2-methoxyphenyl)piperazine (3.92 g, (20 mmol), 1-(2-methoxyphenyl)piperazine hydrochloride (2.29 g, 10 mmol) and methanol (20 ml) was stirred together for 1 h. Sodium cyanoborohydride (0.6 g, 9.6 mmol) was then added portionwise over 5 rain and the mixture stirred for 21 h. The reaction was then diluted with ether (80 ml) and extracted with water (100 ml). The organic phase was separated and the aqueous phase washed with ether. The ether phases were combined, washed with brine, dried ($Na_2SO_4$) and evaporated. The residue was chromatographed on silica and eluted with ether to give two fractions. The first eluted fraction was dissolved in ethanol-chloroform (2:1) and acidified with ethanolic hydrogen chloride to precipitate the cis title compound as its sesqui hydrogen chloride half hydrate (0.3 g), m.p. 125°–132° C.

The second eluted fraction was similarly treated to give the trans title compound as its 1.75 HCl: ¼ $H_2O$ (0.46 g), m.p. 255°–260° C.

EXAMPLE 2

Cis and trans-1-(2-Methoxyphenyl)-4-(1-(4-methylphenyl)cyclohex-4-yl)piperazine

A solution of 1-(2-methoxyphenyl)-4-(1-(4-methylphenyl)cyclohex-1-en-4-yl)piperazine (2.7 g, 7.5 mmol) in methanol (50 ml), water (1 ml) and concentrated hydrochloric acid (1 ml) was hydrogenated at 50 psi (about $3.5 \times 10^5$ $N.m^{-2}$) above atmospheric pressure and 45° C. over 10% Pd/C (2.4 g) for 18 h. The catalyst was then removed by filtration and the filtrate evaporated. The residue was partitioned between dichloromethane (150 ml) and aqueous saturated sodium bicarbonate (100 ml). The organic phase was dried ($Na_2SO_4$) and evaporated. The residue was chromatographed on silica using hexane/ether (2:1):as eluant. The first eluted component was dissolved in ether/dichloromethane (1:1) and acidified with ethereal-HCl. The solvents were evaporated to give the cis title compound as the dihydrochloride (1.08 g), m.p. 199°–200° C.

The second eluted fraction was treated similarly to give the trans title compound as the dihydrochloride (0.74 g), m.p. 200°–205° C.

EXAMPLE 3

Trans- 1-(2-methoxyphenyl)-4-(1-(2-methylphenyl)cyclohex-4-yl)piperazine 1-(2-Methoxyphenyl)-4-(1-(2-methylphenyl)cyclohex-1-en-4-yl)piperazine (0.59 g, 1.36 mmol) was hydrogenated at 41 psi (about $2.8 \times 10^5$ $N.m^{-2}$) above atmospheric pressure in ethanolic HCl (50 ml) using 10% Pd/C as a catalyst, for three days. The volatiles were evaporated in vacuo and the residue was partitioned between dichloromethane (150 ml) and sat $NaHCO_3$ (aq) (100 ml). The organic layer was separated and washed with brine and evaporated in vacuo. The residue was chromatographed on silica using hexane/ether (2:1) as eluant and the slower running compound collected. The white solid was dissolved in ether/dichloromethane (1:1) and acidified to pH 1 with ethereal HCl. The volatiles were removed in vacuo and the white precipitate formed was recrystallised from methanol to give the title compound as the dihydrochloride (0.100 g), m.p. 212° C.

EXAMPLE 4

Cis- and trans-1-(2-methoxyphenyl)-4-(1-(3-methylphenyl)cyclohex-4-yl)piperazine 1-(2-Methoxyphenyl)-4-(1-(3-methylphenyl)cyclohex-1-en-4-yl)piperazine (2.7 g, 7.5 mmol) was hydrogenated at 45 psi (about $2.8 \times 10^5$ $N.m^{-2}$) above atmospheric pressure at 45° C. in methanol (50 ml) and conc.HCl (1 ml), using 10% Pd/C (2.4 g) as a catalyst, overnight. The volatiles were evaporated in vacuo and the residue was partitioned between dichloromethane (150 ml) and sat. $NaHCO_3$ (100 ml). The organic layer was separated and washed with brine and evaporated in vacuo. The residues were chromatographed on silica using hexane/ether (2:1) as eluant and the slower running compound collected. The white solid was dissolved in ether/dichloromethane (1:1) and acidified to pH 1 with ethereal HCl. The volatiles were removed in vacuo and the white precipitate formed was recrystallised from methanol/ether to give the trans title compound as the dihydrochloride; quarter hydrate (0.24 g), m.p. 208°–210° C.

The first eluted fraction was treated similarly to give the cis title compound as the dihydrochloride, quarter hydrate (0.66 g), m.p. 193°–195° C.

EXAMPLE 5

Trans-1-(2-Methoxyphenyl)-4-(1-(4-phenylphenyl)cyclohex-4-yl)piperazine 1-(2-Methoxyphenyl)-4-(1-(4-phenylphenyl)cyclohex-1-en-4-yl)piperazine (2.7 g, 5.4 mmol) was hydrogenated at 50 psi (about $3.5 \times 10^5$ $N.m^{-2}$) above atmospheric pressure at 45° C. in acetic acid (50 ml), using 10% Pd/C (2.4 g) as a catalyst for three days. The volatiles were evaporated in vacuo and the residue was partitioned between dichloromethane (150 ml) and sat. $NaHCO_3$ (200 ml). The organic layer was separated and washed with brine and evaporated in vacuo. The residues were recrystallised from dichloromethane and again from methanol. The white solid was dissolved in ether and acidified to pH 1 with ethereal HCl. The volatiles were removed in vacuo to give the title compound as the one and a half hydrochloride; three quarters hydrate (0.281 g), m.p. 220°–225° C.

EXAMPLE 6

Trans-1-(2-methoxyphenyl)-4-(1-(2-isopropylphenyl)cyclohex-4-yl)piperazine 1-(2-Methoxyphenyl)-4-(2-isopropylphenyl)cyclohex-1-en-4-yl)piperazine (2.5 g, 5.4 mmol) was hydrogenated at 45 psi (about $2.8 \times 10^5$ $N.m^{-2}$) above atmospheric pressure at 45° C. in methanol (50 ml), using 10% Pd/C (2.0 g) as a catalyst, overnight. The volatiles were evaporated in vacuo and the residues were washed with dichloromethane (150 ml) and sat. $NaHCO_3$ (200 ml). The organic layer was washed with brine and evaporated in vacuo. The residues were chromatographed on silica using n-hexane/ether (2:1) as eluant. The white solid was dissolved in ether and acidified to pH 1 with ethereal HCl. The volatiles were removed in vacuo and the product was recrystallised from methanol to give the title compound as the dihydrochloride; hemihydrate (0.372 g), m.p. 200°–202° C.

EXAMPLES 7–12

Following the procedure of Example 1 the following compounds were prepared:

Example 7—trans-1-phenyl-4-(1-phenylcyclohex-4-yl)piperazine as the dihydrochloride, quarter hydrate, m.p. 249° (dec).

Example 8—trans-1-(2-methoxyphenyl)-4-(1-(2-pyridinyl)cyclohex-4-yl)piperazine as the trihydrochloride, monohydrate, m.p. 144° (dec).

Example 9—trans-1-(2-methoxyphenyl)-4-(1-(4-nitrophenyl)cyclohex-4-yl)piperazine as the dihydrochloride, quarter hydrate, m.p. 239°–240° C.

Example 10—cis-1-(2-methoxyphenyl)-4-(3-phenylcyclobut-1-yl)piperazine as the dihydrochloride, one third hydrate, m.p. 238°–241° C. and trans-1-(2-methoxyphenyl)-4-(3-phenylcyclobut-1-yl)piperazine as the dihydrochloride hemihydrate, m.p. 240°–242° C.

Example 11—trans-1-(isoquinolinyl)-4-(4-phenylcyclohex-1-yl)piperazine as the dihydrochloride dihydrate, m.p. 262–264 and cis-1-(isoquinolinyl)-4-(4-phenylcyclohex-1-yl)piperazine as the dihydrochloride, three quarters hydrate, m.p. 241°–268° C.

Example 12—trans-1-(pyrimidin-2-yl)-4-(1-phenylcyclohex4-yl)piperazine as the dihydrochloride three quarters hydrate, m.p. 210°–211° C.

Example 13—trans-1-(2-methoxyphenyl)-4-(3-phenylcyclohex-1-yl)piperazine as the dihydrochloride quarter hydrate, m.p. 203°–205° C.

Example 14—cis-1-(2-methoxyphenyl)-4-(3-phenylcyclohex-1-yl)piperazine as the dihydrochloride, hemihydrate, m.p. 213°–217° C.

EXAMPLE 15

Following the procedure of Example 2 the following compound was prepared:

Trans-1-(2-methoxyphenyl)-4-(1-(4-tert.butylphenyl)cyclohex-4-yl)piperazine as the dihydrochloride quarter hydrate, m.p. 207°–212° C.

EXAMPLE 16

Trans-1-(2-Methoxyphenyl)-4-[1-(2,4-dimethylphenyl)-cyclohex-4-yl]piperazine (a) 1-(2-Methoxyphenyl)-4-[1-(2,4-dimethylphenyl)-cyclohex-1-en-yl)piperazine.

To a solution of 1-(2-methoxyphenyl)-4-[1-hydroxy-1-(2,4-dimethylphenyl)cyclohex-4-yl]piperazine in dichloromethane (anhydrous) at room temperature was added trifluoroacetic acid (8 equivalents). The solution was stirred overnight. Excess trifluoroacetic acid was removed under vacuo and the residue poured into sodium bicarbonate solution. The neutralised aqueous layer was extracted with dichloromethane, washed with salt solution, dried (MgSO$_4$) and filtered. The solvent was removed and the residue purified by silica gel pressure column chromatography using hexane/ether (2/1) as eluant. The solid residue was recrystallised from ether to give the title compound which was converted to its dihydrochloride, m.p. 219° C. (dec.).

(b) Trans-1-(2-methoxyphenyl)-4-[1-(2,4-dimethylphenyl)-cyclohex-4-yl]piperazine The dihydrochloride from (a) above was dissolved in methanol and hydrogenated at 50 psi (about 3.5×10$^5$ N.m$^{-2}$) 45° C. over 10% Pd/C for 18 hours. The catalyst was then removed by filtration and the filtrate evaporated. The residue was partioned between dichloromethane and saturated sodium bicarbonate solution. The organic layer was washed with saturated sodium bicarbonate solution and salt solution, dried (MgSO$_4$) and filtered. The solvent was removed and the oily residue was purified by pressure silica gel column chromatography using hexane/ether (2/1) as eluant to give the title compound. This was convened to the dihydrochloride, m.p. 209° C.

EXAMPLE 17

1-(2-Methoxyphenyl)-4-[1-(2,4-dimethylpyridin-3-yl)-cyclohex-1-en-4-yl]piperazine To a solution of 1-(2-methoxyphenyl)-4-[1-hydroxy-1-(2,4-dimethylpyridin-3-yl)-cyclohex-4-yl]piperazine (0.8 g, 2.0 mmol) in dry THF (70 ml) under argon was added imidazole (0.3 g, 4.4 mmol) followed by methyl oxalyl chloride (0.6 ml, 6.5 mmol). The non-homogeneous reaction mixture was refluxed for 24 hours. The reaction solvent was removed and replaced with anhydrous toluene (50 ml). The reaction mixture was refluxed for a further 48 hours. The solvent was removed and the residue partioned between water and chloroform. The organic layer was removed and washed with saturated NaCl solution. The resulting organic phase was dried (MgSO$_4$) filtered and reduced to an oil. Purification of the oil by silica gel column chromatography eluting with chloroform/methanol (20/1) gave the title product (560 mg) which was dissolved in chloroform to which ethereal HCl was added. The solvent was removed and the residue recrystallised from methanol/ether to give the title compound as the trihydrochloride, 1.75 hydrate, m.p. 215°–216° C.

EXAMPLE 18

Trans-1-(2-methoxyphenyl)-4-[1-(2,4-dimethylpyridin-3-yl)-cyclohex-4-yl]piperazine To an ethanol (100 ml) solution of the cyclohexene product of Example 17 (0.7, 1.85 mmol) was added conc HCl (2 ml) and water (2 ml). Palladium on carbon (10%) (360 mg) was added and the whole hydrogenated in a Parr apparatus at 50 psi (about 3.5×10$^3$ N.m$^{-2}$) and at 40° C. The reduction was allowed to continue overnight before cooling to room temperature. The solids were removed by filtration. Ethanol washings were combined with the filtrate and the solvent removed. The dark material was partioned between chloroform and sodium hydroxide (10%). The organic layer was washed by a further portion of sodium hydroxide before final washing with brine. The organic layer was dried (MgSO$_4$) filtered and reduced to an oil. This was purified by silica gel column chromatography eluting with dichloromethane/methanol (20/1). Fractions containing only the trans isomer were pooled and reduced to dryness. The residue was taken up in chloroform to which ethereal HCl was added. Removal of the volatiles gave a solid which was recrystallised from methanol/ether to give the title compound as the trihydrochloride, 0.5 methanolate, m.p. 172°–174° C.

EXAMPLE 19

1-(2-Methoxyphenyl)-4-[1-(3,5-dimethylpyridin-2-yl)-cyclohex-1-en-4-yl]piperazine Methyloxalyl chloride (0.35 ml) was added to a mixture of 1-(2-methoxyphenyl)-4-[1-hydroxy-1(3,5-dimethylpyridin-2-yl)-cyclohex-4-yl]piperazine (0.7 g, 1.8 mmol) and imidazole (0.25 g) in THF (15 ml) at reflux. Heating was continued overnight when the solvent was evaporated in vacuo and replaced with toluene (15 ml). The mixture was heated under reflux overnight, then, when cool, added to dilute NaOH (aq) and extracted by ether (3×50 ml). The combined organic extracts were washed with brine (50 ml) and water (50 ml), dried over magnesium sulphate and evaporated to dryness. The crude product was chromatographed (SiO$_2$, 2% methanol in dichloromethane) giving the title compound (0.42 g) which was recrystallised from hexane then treated with ethanolic HCl to give the title compound as the trihydrochloride 2.25 hydrate, m.p. 235°–236° C.

EXAMPLE 20

Trans-1-(2-Methoxyphenyl)-4-[1-(3,5-dimethylpyridin-2-yl)-cyclohex-4-yl]piperazine The alkene product of Example 19 (0.85 g, 2.25 mmol) in ethanol (100 ml), conc. HCl (2 ml) and water (2 ml) was hydrogenated over 10% palladium on carbon (0.5 g) at 50 psi (about 3.5×10$^3$ N.m$^{-2}$) and at 50° C. overnight. Removal of catalyst by filtration was followed by solvent evaporation and the residue was partitioned between 10% NaOH solution and dichloromethane. The organic extracts were washed with brine, dried over MgSO$_4$ and evaporated to dryness. Purification was by column chromatography (SiO$_2$, 2% MeOH/CH$_2$Cl$_2$) which afforded the trans-isomer as the minor isomer (0.1 g 12%). The title compound hydrochloride was formed in ethereal HCl and recrystallisation from ethanol/ether gave the trihydrochloride hydrate, m.p. 240°–242° C.

EXAMPLE 21

Trans-1-(2-methoxyphenyl)-4-[1-(2-methoxy-4-methylphenyl)-cyclohex-4-yl]piperazine (a) A mixture of 4-(2-methyl-6-methoxyphenyl)-cyclohex-3-en-1-one and 4-(4-methyl-6-methoxyphenyl)-cyclohex-3-en-1-one (2.8 g, 13 mmol), (2-methoxyphenyl)piperazine (2.5 g, 13 mmol) and glacial acetic acid (1.2 ml) were stirred in dichloromethane (20 ml) for 30 minutes. Sodium triacetoxyborohydride (2.75 g, 13 mmol) was added and the mixture stirred at room temperature overnight. Pouring into aqueous sodium bicarbonate solution was followed by extraction by dichloromethane (3×25 ml) and the combined organic extracts were washed with water (2×50 ml) and brine (50 ml). Drying over magnesium sulphate was followed by solvent removal in vacuo and the residue purified by column chromatography (2% methanol in dichloromethane) to give a mixture of 1-(2-methoxyphenyl)-4-[1-(2-methoxy-6-methylphenyl) cyclohex-1-en-4-yl]piperazine and 1-(2-methoxyphenyl)-4-[1-(2-methoxy-4-methylphenyl)cyclohex-1-en-4-yl] piperazine (1.78 g).

(b) A mixture of the dihydrochlorides of 1-(2-methoxyphenyl)-4-[1-(2-methoxy-6-methylphenyl)cyclohex-1-en-4-yl]piperazine and 1-(2-methoxyphenyl)-4-[1-(2methoxy-4-methylphenyl)cyclohex-1-en-4-yl] piperazine (1.78 g) in methanol (75 ml) was hydrogenated over palladium on charcoal (10% Pd/C, 1.5 g) at 50° psi (about 3.5×10$^5$ N.m$^{-2}$)at 45° C. overnight. The catalyst was removed by filtration and solvent removed in vacuo. The residue was partitioned between dilute NaOH (10% aq) and dichloromethane and the organic phase washed with water and brine, dried over MgSO$_4$ and evaporated to dryness. Purification of the residue was by means of column chromatography, first using ether/hexane allowing isolation of the cis-isomer then again using 2% methanol in dichloromethane. This allowed separation of the trans title compound from the 2,6-alkene starting material.

The title compound 0.25 hydrate had, m.p.=91°–93° C.

We claim:

1. A compound according to the formula

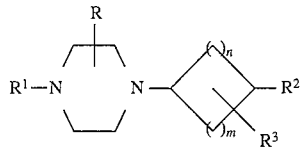

wherein:

R and R$^3$ are H;

n and m are each 2 or n is 1 and m is 3;

R$^1$ and R$^2$ are independently phenyl, optionally substituted by 1 or 2 substituents selected from lower alkyl, lower alkoxy, nitro and phenyl;

phenylloweralkyl;

pyridinyl, optionally substituted by lower alkyl and lower alkoxy;

pyrimidinyl, or isoquinolinyl;

a cis or trans isomer;

or a pharmaceutically acceptable salt thereof.

2. A compound claimed in claim 1 wherein n and m are both 2.

3. A compound as claimed in claim 1 wherein R$^1$ is an optionally substituted phenyl radical.

4. A compound as claimed in claim 1 wherein R$^1$ is o-(lower)alkoxyphenyl.

5. A compound as claimed in claim 1 wherein R$^2$ is phenyl or pyridyl optionally substituted by lower alkyl.

6. A compound as claimed in claim 1 which is cis- or trans-1-(2-methoxyphenyl)-4-(1-phenylcyclohex-4-yl)piperazine, cis or trans-1-(2-methoxyphenyl)-4-(1-(4-methylphenyl)cyclohex-4-yl)piperazine, trans-1-(2-methoxyphenyl-4-(1-(2-methylphenyl)cyclohex-4-yl)piperazine, cis- or trans-1-(2-methoxyphenyl)-4-(1-(3-methylphenyl)cyclohex-4-yl)piperazine, trans-1-(2-methoxyphenyl)-4-(1-(4-phenylphenyl)cyclohex-4-yl)piperazine, trans-1-(2-methoxyphenyl)-4-(1-(2-isopropylphenyl)cyclohex-4-yl)piperazine, trans-1-phenyl-4-(1-phenylcyclohex-4-yl)piperazine trans-1-(2-methoxyphenyl)-4-(1-(2-pyridinyl)cyclohex-4-yl)piperazine, trans-1-(2-methoxyphenyl)-4-(1-(4-nitrophenyl)cyclohex-4-yl)piperazine, cis or trans-1-(2-methoxyphenyl)-4-(3-phenylcyclobut-1-yl)piperazine, cis or trans-1-(isoquinolinyl)-4-(4-phenylcyclohex-1-yl)piperazine, trans-1-(pyrimidin-2-yl)-4-(1-phenylcyclohex-4-yl)piperazine, trans-1-(2-methoxyphenyl)-4-(3-phenylcyclohex-1-yl)piperazine, cis-1-(2-methoxyphenyl)-4-(3-phenylcyclohex-1-yl)piperazine, trans-1-(2-methoxyphenyl)-4-(1(4-tert.butylphenyl)cyclohex-4-yl)piperazine, trans-1-(2-methoxyphenyl)-4-[1-(2,4-dimethylphenyl)-cyclohex-4-yl] piperazine, trans-1-(2-methoxyphenyl)-4-[1-(2,4-dimethylpyridin-3-yl)-cyclohex-4-yl]piperazine, trans-1-(2-methoxyphenyl)-4-[1-(3,5-dimethylpyridin-2-yl)-cyclohex-4-yl]piperazine or trans-1-(2-methoxyphenyl)-4-[1-(2-methoxy-4-methylphenyl)-cyclohex-4-yl]piperazine or a pharmaceutically acceptable acid addition salt thereof.

7. A pharmaceutical composition for use as a 5-HT$_{1A}$ antagonist comprising a compound claimed in claim 1 in association with a pharmaceutically acceptable carrier.

* * * * *